United States Patent
Mellis

(10) Patent No.: US 7,279,282 B2
(45) Date of Patent: Oct. 9, 2007

(54) METHODS FOR IDENTIFYING A CANDIDATE FOR TREATMENT OF OBESITY

(76) Inventor: Scott Mellis, 33 Woodhollow Ln., New Rochelle, NY (US) 10804

( * ) Notice: Subject to any disclaimer, the term of this patent is extended or adjusted under 35 U.S.C. 154(b) by 74 days.

(21) Appl. No.: 11/177,860

(22) Filed: Jul. 8, 2005

(65) Prior Publication Data

US 2006/0008832 A1    Jan. 12, 2006

Related U.S. Application Data

(60) Provisional application No. 60/586,983, filed on Jul. 9, 2004.

(51) Int. Cl.
*C12Q 1/68* (2006.01)
*C12P 19/34* (2006.01)
*A01N 37/18* (2006.01)
*A61K 38/00* (2006.01)

(52) U.S. Cl. .................. 435/6; 435/91.1; 435/91.2; 514/2

(58) Field of Classification Search .............. None
See application file for complete search history.

(56) References Cited

U.S. PATENT DOCUMENTS 6,472,178 B1 * 10/2002 Fandl et al. ............ 435/69.4
6,565,869 B1 *  5/2003 Ciliberto et al. ............ 424/423
2004/0082000 A1    4/2004 Stanton, Jr.

FOREIGN PATENT DOCUMENTS

WO         WO 01/89550         11/2001

OTHER PUBLICATIONS

Klitz et al. Tissue Antigens 2003. 62:296-307.*
Ghodke et al. Eur. J. Epidemiol. 2005. 20: 475-488.*
Vergara et al. Brain Res. Rev. 2004. 47:161-173.*
Heward et al. Eur. J. Immunogenet. 2002. 29: 47-52.*
Motala et al. Clin. Diag. Lab. Immunol. 2005. 12:213-217.*
Voorter et al. Human Immunol. 2005. 66: 826-835.*
Perez-Luque et al. Hum. Immunol. 2003. 64: 110-118.*
Gibert, M., et al., (2003) Human Immunology 64(10):930-935.
Price, P., et al., (2001) Immunology and Cell Biology 79(6):602-606.

* cited by examiner

*Primary Examiner*—Janet L. Andres
*Assistant Examiner*—Chang-Yu Wang

(57) ABSTRACT

Methods of identifying human subjects for treatment of obesity or an obesity-related condition with ciliary neurotrophic factor (CNTF) or a CNTF-related molecule, such as Axokine®, based on the presence of human leukocyte antigen (HLA) DRβ1 allele 1501 or the absence of HLA DRβ1 allele 0701.

8 Claims, 2 Drawing Sheets

METHODS FOR IDENTIFYING A CANDIDATE FOR TREATMENT OF OBESITY

RELATED APPLICATIONS

This application claims the benefit under 35 USC 119(e) to U.S. Ser. No. 60/586,983 filed Jul. 9, 2004, which application is incorporated by reference in its entirety.

BACKGROUND

1. Technical Field

This invention relates to methods of identifying a human subject for treatment of obesity based on genetic information, including specific gene sequence alleles within the genome of a patient which effects treatment response.

2. Statement of Related Art

Many drugs or other treatments are known to have highly variable safety and efficacy in different individuals. A consequence of such variability is that a given drug or other treatment may be effective in one individual, and ineffective in another individual. Thus, administering a drug to an individual in whom the drug is ineffective results in unnecessary expense and wasted time during which the patient's condition may significantly worsen. Also, administering a drug to a patient in whom the drug is not tolerated could result in a direct worsening of the patient's condition.

For some drugs, over 90% of the measurable variation in selected pharmacokinetic parameters has been shown to be heritable. For a limited number of drugs, DNA sequence variances have been identified in specific genes that are involved in drug action or metabolism, and these variances have been shown to account for the variable efficacy or safety of the drugs in different individuals.

Ciliary neurotrophic factor (CNTF) is a protein that is required for the survival of embryonic chick ciliary ganglion neurons in vitro (Manthorpe et al. (1980) J. Neurochem. 34:69-75). CNTF variants having specific physical, biochemical and pharmacological properties are known. For example, Axokine® (SEQ ID NO:1-2) is a modified CNTF molecule with improved physical and chemical properties, which retains the ability to interact with and activate the CNTF receptor. (Panayotatos et al. (1993) J. Biol. Chem. 268: 19000-19003). Axokine® has been found to be effective for the treatment of obesity.

BRIEF SUMMARY OF THE INVENTION

Treatment of obesity with Axokine® was tested in a large Phase III clinical trial (study AX-15-OB-0008). Definitive evidence of efficacy was observed; however approximately two-thirds of subjects developed antibodies against Axokine® which was associated with lower degrees of overall weight loss.

Immunologists have been exploring mechanisms responsible for immunogenicity of exogeneously administered proteins for many years. It is widely believed that Class II HLA molecules such as HLA DR beta 1 are responsible for key steps in the initiation of antibody responses against such proteins. It is believed that diversity in these alleles across individuals in a population may differences in immune responses to various proteins.

As part of the Axokine® studies, pharmacogenomic substudies were conducted, including analysis of DNA polymorphisms from trial participants. As a result of these studies, the inventors have identified an alleles on HLA DR beta 1 that are predicative of the ability of a subject to respond to Axokine® treatment with medically meaningful weight loss, e.g., 5% or greater of initial body weight.

Accordingly, in a first aspect, the invention features a method of identifying a human subject suffering from a CNTF-related condition as a candidate for treatment with CNTF or a CNTF-related molecule, comprising (a) obtaining a DNA sample from a candidate subject; (b) determining the presence or absence of a specific human leukocyte antigen DR beta 1 allele (HLA DRβ1 allele) correlated with a response to CNTF or a CNTF-related molecule, wherein the presence or absence of a specific HLA DRβ1 allele identifies a candidate for treatment with CNTF or a CNTF-related molecule. In a preferred embodiment, the HLA DRβ1 allele present is 1501. In another preferred embodiment, the HLA DRβ1 allele absent is 701. In another preferred embodiment HLA DRβ1 allele 1501 is present and 701 is absent. In a preferred embodiment, the CNTF-related molecule is Axokine®).

In a preferred embodiment, the condition being treated is obesity. In other embodiments, the condition being treated is an obesity-related condition such as metabolic syndrome (hyperglycemia, hyperlipidemia, hypercholesterolemia, hypertriglyceridemia, hyperinsulinemia and/or hypertension); diabetes, diabetic angiopathy, atherosclerosis, diabetic nephropathy, diabetic neuropathy, diabetic ocular complications such as retinopathy, cataract formation and glaucoma; dyslipidemia, polycysitic ovarian syndrome, etc.

When the condition being treated is obesity, a response is measured by weight loss. In a preferred embodiment, the subject identified is a candidate for treatment is predicted to achieve a greater weight loss than a non-treated obese subject. In one embodiment, the weight loss is a medically meaningful weight loss of 5% or greater relative of initial body weight. In another embodiment, the subject is identified as a member of a population that has a statistically significant increase in the percentage of subjects who lose medically meaningful weight of 5% or more of initial body weight compared to a placebo. In a preferred embodiment, the weight loss response is achieved over a period of 1 month or greater; 2 months or greater; or 3 months or greater.

All the methods of treating described herein include administration of CNTF or a CNTF-related molecule by any method known to those skilled in the art including subcutaneous, intramuscular, intradermal, transdermal, intraperitoneal, intravenous, intranasal, intrathecal, intraocular, or oral routes of administration.

In a second aspect, the invention features a method of treating obesity, or an obesity-related condition, comprising (a) identifying a subject having an allele identified with medically meaningful weight loss in response to treatment of obesity or an obesity-related condition with CNTF or a CNTF-related molecule; and (b) administering CNTF or a CNTF-related molecule such that a medically meaningful weight loss is achieved. In a preferred embodiment, the allele is 1501 of HLA DRβ1 (DRβ1 allele 1501). In a preferred embodiment, the CNTF-related molecule is Axokine®. A medically meaningful weight loss is a weight loss of 5% or more of initial body weight.

In a third aspect, the invention features a method for determining whether a candidate subject suffering from obesity or a obesity-related disorder will respond to treatment with CNTF or a CNTF-related molecule, comprising detecting HLA DRβ1 allele 1501 in a nucleic acid sample from the candidate subject, wherein detection of HLA DRβ1 allele 1501 indicates that the subject is a desirable candidate for treatment with CNTF or a CNTF-related molecule. The detection of HLA DRβ1 allele 1501 may be performed by any method known to the art, including allele specific oligonucleotide hybridization; size analysis; sequencing; hybridization; 5' nuclease digestion; single-stranded conformation polymorphism; allele specific hybridization; primer specific extension; and oligonucleotide ligation assay. In specific embodiments, the nucleic acid sample is subject to an amplification step prior to or in conjunction to detection. In a preferred embodiment, the response to treatment with CNTF or a CNTF-related molecule is determined by weight loss relative to the initial body weight. In other embodiments, response to treatment with CNTF or a CNTF-related molecule is determined by reduction in blood glucose, lipid and/or cholesterol levels, decreased insulin resistance, or improvement in other parameters recognized by one of skill in the art as a desirable response.

In a fourth aspect, the invention features a method for determining whether a candidate subject suffering from obesity or a obesity-related disorder is expected to respond to treatment with CNTF or a CNTF-related molecule, comprising detecting HLA DRβ1 allele 0701 in a nucleic acid sample from the candidate subject, wherein detection of HLA DRβ1 allele 0701 indicates that the subject is not a desirable candidate for treatment with CNTF or a CNTF-related molecule. A subject that is not a desirable candidate for treatment with CNTF or a CNTF-related molecule is one which is not expected lose a medically meaningful amount of weight.

In a fifth aspect, the invention features a method of selecting a population of subjects for treatment of obesity or an obesity-related condition, comprising (a) obtaining DNA from a candidate subject; (b) determining the presence and/or absence or one or more preidentified HLA DRβ1 alleles, wherein a candidate subject having the presence of a desirable HLA DRβ1 allele and/or absence of an undesirable HLA DRβ1 allele is selected as a member of the population.

Other objects and advantages will become apparent from a review of the ensuing detailed description.

DETAILED DESCRIPTION

Figure 1:
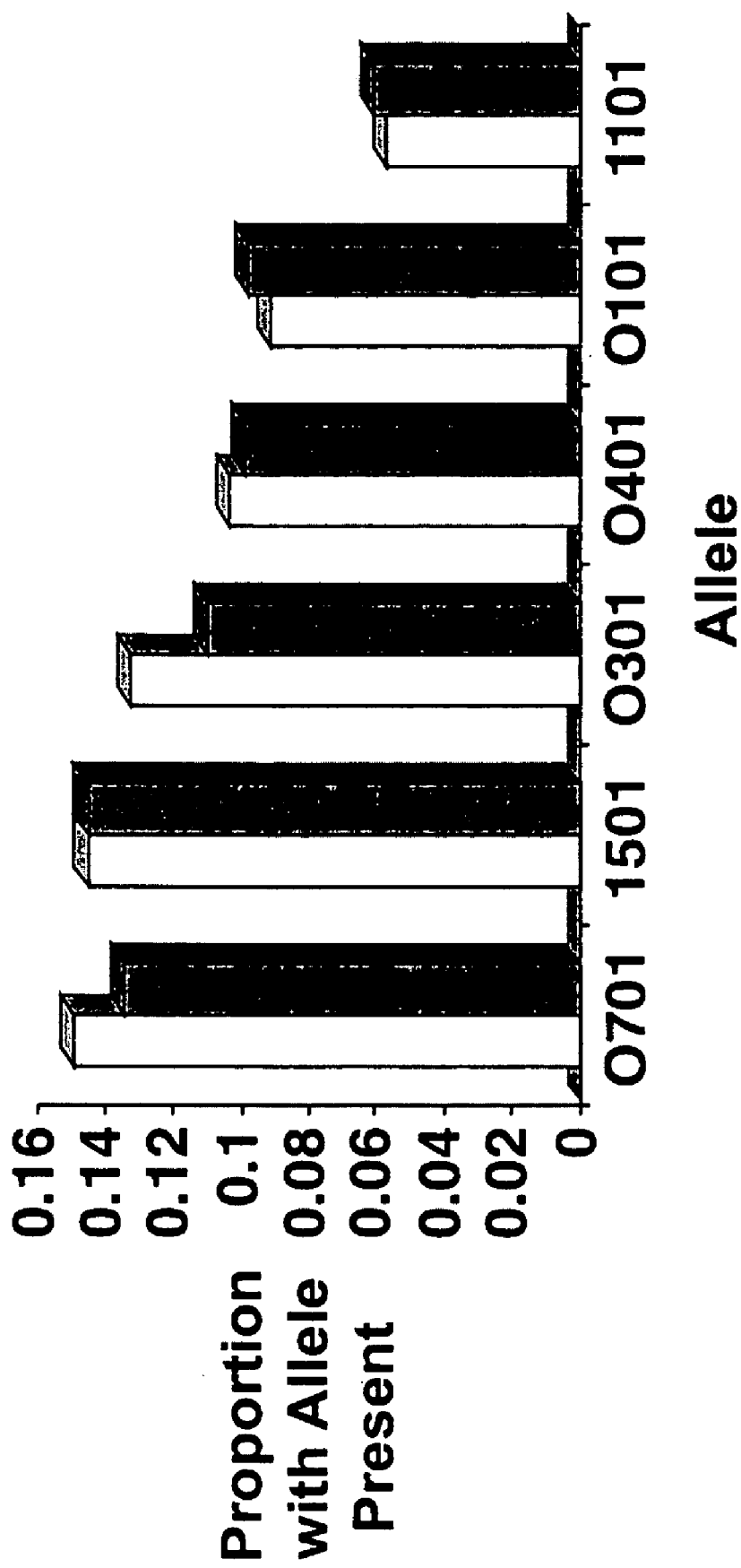
FIG. 1 is a bar graph showing the allele frequency of the most common HLA DRβ1 alleles examined in the general population (□) and the study population (■).

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, references to "a method" include one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

General Description

The present invention provides a method of identifying a human subject likely to benefit from treatment of obesity or an obesity-related condition with a CNTF-related drug, where the identification of the subject is based upon their genotype. More specifically, the invention describes at least one genetic allele for optimizing efficacy and/or safety of drug therapy with a CNTF-related drug. The method of the invention allows identification of human subjects most likely to receive maximum health benefits from treatment with a CNTF-related drug. Methods for identifying genetic variances and the presence or absence of specific alleles are known in the art, see for example U.S. 2004/0082000, which publication is herein specifically incorporated by reference in its entirety. In related aspects, the invention features methods of identifying a human subject who should avoid treatment regimens involving a CNTF-related molecule as a person unlikely to benefit from such treatment.

DEFINITIONS

By the term "effective dose" or "therapeutically effective dose" is meant a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding). For example, when the condition being treated is obesity, a therapeutically effective amount of CNTF or a CNTF-related molecule is an amount which results in a medically meaningful or statistically significant weight loss. One of skill in the art understands how to determine whether weight loss is statistically significant. Generally, statistical significance is recognized at p values of 0.05, 0.01, or 0.001.

The terms "CNTF-related diseases or condition" are commonly recognized in the art and designate the presence of signs and/or symptoms in an individual or patient that are generally recognized as abnormal. Diseases or conditions may be diagnosed and categorized based on pathological or undesirable changes. In a preferred embodiment, the disease or condition of interest is obesity. In another embodiment, the condition is metabolic syndrome (also known as syndrome X), generally defined as involving three of more of central/abdominal obesity, fasting triglycerides greater than or equal to 150 mg/dL, HDL cholesterol less than 40 mg/dl (men) or 50 mg/dL (women), blood pressure greater than or equal to 130/85, and/or fasting glucose greater than or equal to 110 mg/dL. In another embodiment, the condition is non-insulin dependent diabetes mellitus (type II diabetes or NIDDM), diabetic angiopathy, atherosclerosis, diabetic nephropathy, diabetic neuropathy, and diabetic ocular complications such as retinopathy, cataract formation and glaucoma; dyslipidemia, polycysitic ovarian syndrome, hyperglycemia, hyperlipidemia, hypercholesterolemia, hypertriglyceridemia, hyperinsulinemia, and/or hypertension. In connection with the methods of this invention, unless otherwise indicated, the term "suffering from a disease or condition" means that a person is either presently subject to the signs and symptoms, or is more likely to develop such signs and symptoms than a normal person in the population.

The term "allele" refers to the different sequence variants found at different polymorphic regions. The sequence variants may be single or multiple base changes, including without limitation insertions, deletions, or substitutions, or may be a variable number of sequence repeats.

The term "allelic pattern" refers to the identity of an allele or alleles at one or more polymorphic regions. For example, an allelic pattern may consist of a single allele at a polymorphic site or either a homozygous or heterozygous state at a single polymorphic site.

In the context of this invention, the term "haplotype" refers to a cis arrangement of two or more polymorphic nucleotides, i.e., variances, on a particular chromosome, e.g., in a particular gene. The haplotype preserves information about the phase of the polymorphic nucleotides—that is, which set of variances were inherited from one parent, and which from the other. A genotyping test does not provide information about phase. For example, an individual heterozygous at nucleotide 25 of a gene (both A and C are present) and also at nucleotide 100 (both G and T are present) could have haplotypes 25A-100G and 25C-100T, or alternatively 25A-100T and 25C-100G. Only a haplotyping test can discriminate these two cases definitively. Haplotypes may also be determined by detection of the expressed gene products of the HLA locus via means known to the art, including, for example, serology.

The terms "variances", "variants" and "polymorphisms", as used herein, may also refer to a set of variances, haplotypes or a mixture of the two, unless otherwise indicated. Further, the term variance, variant or polymorphism (singular), as used herein, also encompasses a haplotype unless otherewise indicated. This usage is intended to minimize the need for cumbersome phrases such as: " . . . measure correlation between drug response and a variance, variances, haplotype, haplotypes or a combination of variances and haplotypes . . . ", throughout the application. Instead, the italicized text in the foregoing sentence can be represented by the word "variance", "variant" or "polymorphism". Similarly, the term "genotype", as used herein, means a procedure for determining the status of one or more variances in a gene, including a set of variances comprising a haplotype. Thus phrases such as " . . . genotype a patient . . . " refer to determining the status of one or more variances, including a set of variances for which phase is known (i.e. a haplotype).

In preferred embodiments of this invention, the frequency of the variance or variant form of the gene in a population is known. Measures of frequency known in the art include "allele frequency", namely the fraction of genes in a population that have one specific variance or set of variances. The allele frequencies for any gene should sum to 1. Another measure of frequency known in the art is the "heterozygote frequency" namely, the fraction of individuals in a population who carry two alleles, or two forms of a particular variance or variant form of a gene, one inherited from each parent. Alternatively, the number of individuals who are homozygous for a particular form of a gene may be a useful measure.

The term "genotype" in the context of this invention refers to the alleles present in DNA from a subject or patient, where an allele can be defined by the particular nucleotide(s) present in a nucleic acid sequence at a particular site(s).

The process of genotyping involves using diagnostic tests for specific variances that have already been identified. It will be apparent that such diagnostic tests can only be performed after variances and variant forms of the gene have been identified. Identification of new variances can be accomplished by a variety of methods, alone or in combination, including, for example. DNA sequencing, SSCP (sequence specific oligonucleotide hybridization, sequence specific DNA amplification), heteroduplex analysis, denaturing gradient gel electrophoresis (DGGE), heteroduplex cleavage (either enzymatic as with T4 Endonuclease 7, or chemical as with osmium tetroxide and hydroxylamine), computational methods (described herein), and other methods described herein as well as others known to those skilled in the art.

In the context of this invention, the term "analyzing a sequence" refers to determining at least some sequence information about the sequence, e.g., determining the nucleotides present at a particular site or sites in the sequence, particularly sites that are known to vary in a population, or determining the base sequence of all or of a portion of the particular sequence.

In this regard, "population" refers to a defined group of individuals or a group of individuals with a particular disease or condition or individuals that may be treated with a specific drug identified by, but not limited to geographic, ethnic, race, gender, and/or cultural indices. In most cases a population will preferably encompass at least ten thousand, one hundred thousand, one million, ten million, or more individuals, with the larger numbers being more preferable. In preferred embodiments of this invention, the population refers to individuals with a specific disease or condition that may be treated with a specific drug. In embodiments of this invention, the allele frequency, heterozygote frequency, or homozygote frequency of a specific variance or variant form of a gene is known. In preferred embodiments of this invention, the frequency of one or more variances that may predict response to a treatment is determined in one or more populations using a diagnostic test.

As used herein, the terms "effective" and "effectiveness" includes both pharmacological effectiveness and physiological safety. Pharmacological effectiveness refers to the ability of the treatment to result in a desired biological effect in the patient, e.g., weight loss. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the unstratified population. (Such a treatment may be ineffective in a subgroup that can be identified by the presence of one or more sequence variances or alleles.) "Less effective" means that the treatment results in a therapeutically significant lower level of pharmacological effectiveness and/or a therapeutically greater level of adverse physiological effects, e.g., greater liver toxicity.

CNTF and CNTF Variants

The method of the invention encompasses the administration of [DS1]CNTF, or a modified variant thereof. In a preferred embodiment, the method of the invention is practiced with CNTF or a modified CNTF. A modified CNTF molecule termed Axokine™ (SEQ ID NO:1-2) (Regeneron Pharmaceuticals, Inc.) described in U.S. Pat. No. 6,472,178, the disclosure of which is herein specifically incorporated by reference. Modified CNTF molecules useful in the method of the present invention include, for example, RG297, RG242, rHCNTF, rHCNTFΔ13, Ax-1, Ax-13, Ax-15, or any other modified CNTF that enhances the molecules therapeutic properties.

The CNTF and modified CNTF molecules useful for practicing the present invention may be prepared by cloning and expression in a prokaryotic or eukaryotic expression system as described, for example in Masiakowski et al. (1991) J. Neurosci. 57:1003-1012 and in WO 91/04316. The recombinant neurotrophin gene may be expressed and purified utilizing any number of methods.

Methods of Detecting Alleles

An allele associated with weight loss response to Axokine® treatment can be detected by any of a variety of available techniques, including: 1) performing a hybridization reaction between a nucleic acid sample and a probe that is capable of hybridizing to the allele; 2) sequencing at least a portion of the allele; or 3) determining the electrophoretic mobility of the allele or fragments thereof (e.g., fragments generated by endonuclease digestion). The allele can optionally be subjected to an amplification step prior to performance of the detection step. Preferred amplification methods are selected from the group consisting of: the polymerase chain reaction (PCR), the ligase chain reaction (LCR), strand displacement amplification (SDA), cloning, and variations of the above (e.g. RT-PCR and allele specific amplification). Oligonucleotides necessary for amplification may be selected for example, from within the HLA DRβ1 gene loci, either flanking the marker of interest (as required for PCR amplification) or directly overlapping the marker (as in ASO hybridization). In a particularly preferred embodiment, the sample is hybridized with a set of primers, which hybridize 5' and 3' in a sense or antisense sequence to the allele of interest, and is subjected to a PCR amplification.

An allele of interest may also be detected indirectly, e.g. by analyzing the protein product encoded by the DNA. For example, where the marker in question results in the translation of a variable protein, the protein can be detected by any of a variety of protein detection methods. Such methods include immunodetection and biochemical tests, such as size fractionation, where the protein has a change in apparent molecular weight either through truncation, elongation, altered folding or altered post-translational modifications.

Alleles Associated with Axokine®-Induced Weight Loss

An allele whose presence is identified with individuals responding to obesity treatment with Axokine® with a medically meaningful weight loss is considered a desirable allele. Examples of type of allele include allele 1501 of HLA DRβ1.

An allele whose presence is identified with individuals not responding to obesity treatment with Axokine® with a medically meaningful weight loss is considered an undesirable allele. Examples of type of allele include allele 0701 of HLA DRβ1.

Kits and Diagnostic Products and Methods

The present invention is useful in a diagnostic product to detect the presence of allele 1501 or structurally related alleles. Accordingly, the invention encompasses the use of diagnostic kits based on a variety of methodologies, e.g., sequence, chip, mass-spectroscopy, which are capable of finding signature sequences indicative of the HLA alleles described herein or closely related molecules. The invention also provides an article of manufacturing comprising packaging material and a pharmaceutical agent contained within the packaging material, wherein the pharmaceutical agent comprises means for detecting the presence of allele 1501 or structurally related alleles, and packaging material comprises a label or package insert which indicates that the detection means can be used to identify a candidate subject suitable for treatment of obesity with Axokine®.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Determination of HLA DR Beta 1 Allele Correlating with Weight Loss Resulting from Axokine® Treatment.

Selection of treatment population. Male and non-pregnant, non-lactating female subjects, aged 18 to 70 years, with a BMI (body mass index: weight/[height]$^2$) of 27 to 55 kg/m$^2$, inclusive, were selected for the study as follows: subjects having a BMI of 30 to 55 kg/m$^2$ in the absence of obesity-related risk factors or having a BMI of 27 to 55 kg/m$^2$ in the presence of obesity-related risk factors, such as hypertension, dyslipidemia, etc.

Blood specimens for the pharmacogenetic analysis were obtained with consent from approximately 530 patients who participated in the Axokine® clinical studies. These samples were acquired and DNA was purified and stored. Samples were coded via a process known as "de-identification".

The initial genotyping analyses focused on HLA DRβ1. This locus is highly polymorphic and there are differences in frequencies of various alleles between populations of different ethnic background. In these clinical trials, approximately 85% of subjects were of European-American origin; therefore, only samples from these patients were genotyped, as numbers from other ethnic groups were considered too small to enable statistically meaningful results to be obtained. Aliquots (50 ug) of purified DNA from each subject (n=562) were shipped frozen and analyzed by amplification and sequencing. Coding on samples will remain "as-is" in "de-identified" state.

Genotyping and Data Reporting. High resolution sequence based genotyping was performed for HLA DR beta1 allele identification (4 digit) on all specified samples.

Results. High resolution of HLA DRβ1 was performed for every study subject of European-American descent who had provided a DNA specimen. In an initial analysis, the frequency of the most common HLA DRβ1 alleles (alleles 0701, 1501, 0301, 0401, 0101, and 1101) were compared between the Axokine® study group and a published reference population (Klitz et al. (2003) Tissue Antigens 62:296-307, herein specifically incorporated by reference in its entirety). The allele frequency in the sample population was similar to that of the general population (FIG. 1).

Figure 2:
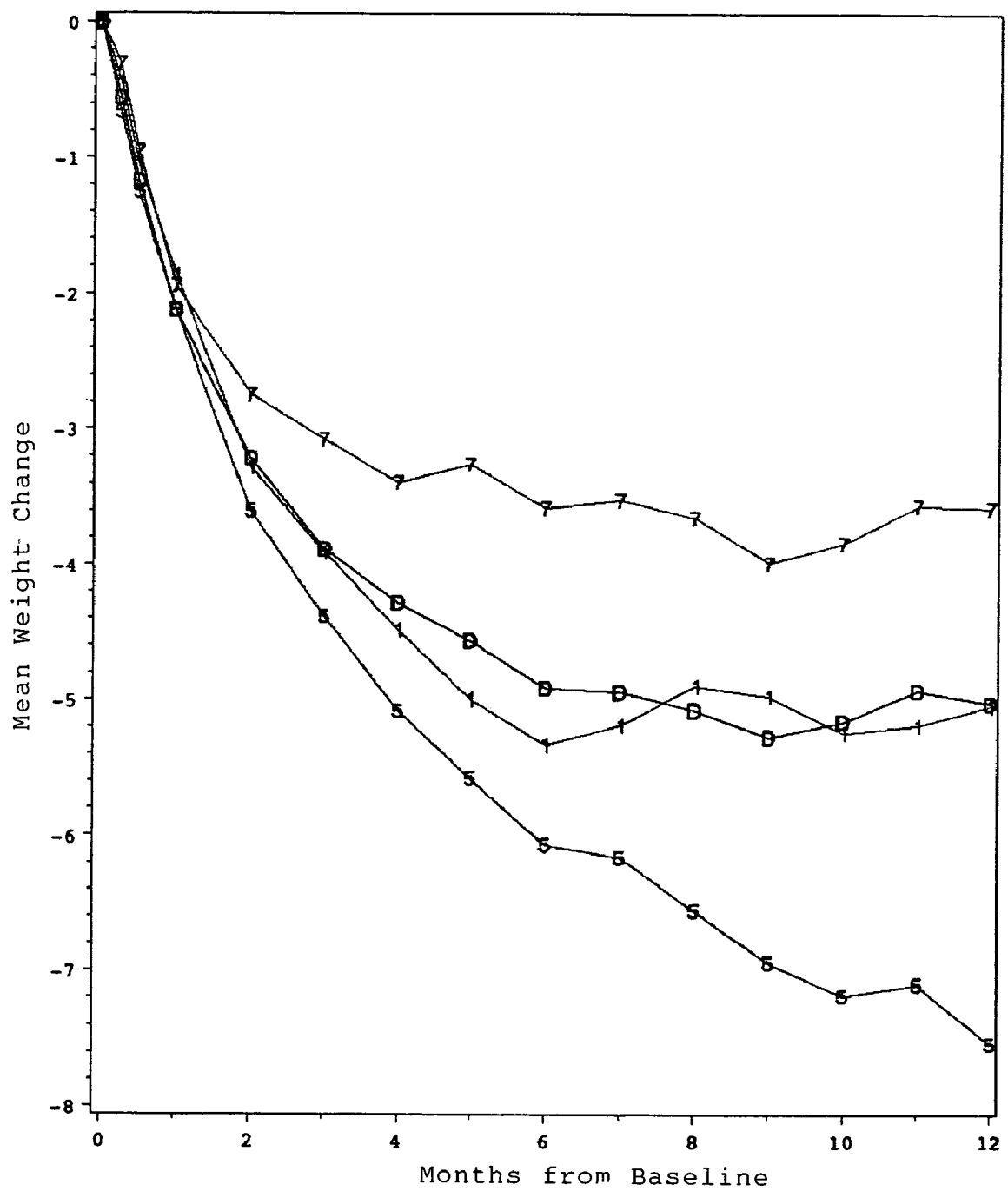
FIG. 2 is a graph showing mean weight loss over time for four Axokine®) treated groups: D=DNA from all treated subjects; 1=DRβ1 allele 1101; 7=DRβ1 allele 0701; and 5=DRβ1 allele 1501.

In the next analysis, the proportion of subjects with at least one of the common alleles was compared between subjects who tested positive for Axokine® antibodies at some point during the study. The subpopulation having allele 1501 composed about 25% of the population and was found to correlate significantly with weight loss resulting from Axokine® treatment. FIG. 2 shows that allele 1501 positive subjects had a mean weight loss of 2.5 kg relative to the mean weight loss of group D and 4.5 kg relative to the group expressing allele 0701. The results are further summarized in Table 1 for allele 1501 positive and negative subjects relative to their respective placebo-treated groups. 5% responders are subject who lost 5% or more of their initial body weight; 10% responders are subjects who lost 10% or more of their initial body weight.

TABLE 1

|  | 1501 positive | | 1501 negative | |
| --- | --- | --- | --- | --- |
|  | Axokine®-Treated n = 92 | Placebo n = 25 | Axokine®-Treated n = 248 | Placebo n = 86 |
| Mean Weight Loss (lbs) | 16.6 | 2.0 | 9.0 | 7.2 |
| Median Weight Loss (lbs) | 12.1 | 4.0 | 6.4 | 3.1 |
| 5% Responders | 51% | 24% | 34% | 33% |
| 10% Responders | 33% | 4% | 19% | 12% |

The invention claimed is:

1. A method of identifying a human subject for treatment of a CNTF-related condition with CNTF or a CNTF-related molecule, comprising:
(a) obtaining a DNA sample from a candidate subject;
(b) determining the presence or absence of human leukocyte antigen DR beta 1 allele (HLA DRβ1 allele), wherein a subject having HLA DRβ1 1501 allele is a candidate for treatment with CNTF or a CNTF-related molecule, wherein the CNTF-related molecule is Axokine® (SEQ ID NO:1-2), and the CNTF-related condition is obesity.

2. The method of claim 1, further comprising (c) treating the identified subject with CNTF or a CNTF-related molecule such that the CNTF-related condition is ameliorated or inhibited.

3. The method of claim 2, wherein treatment results in weight loss.

4. The method of claim 3, wherein weight loss is 5% or more of initial body weight.

5. The method of claim 2, wherein treating with CNTF or a CNTF-related molecule comprises administration via subcutaneous, intramuscular, intradermal, intraperitoneal, intravenous, intranasal, or oral routes of administration.

6. A method of selecting a population of subjects for treatment of obesity or an obesity-related condition with CNTF or a CNTF-related molecule, comprising:
(a) obtaining a biological sample from a candidate subject;
(b) determining the presence and/or absence or one or more preidentified HLA DRβ1 alleles in the biological sample, wherein a candidate subject having the presence of HLA DRβ1 1501 allele and/or absence of HLA DRβ1 701 allele is selected as a member of the population, wherein the CNTF-related molecule is Axokine® (SEQ ID NO:1-2).

7. The method of claim 6, wherein the presence or absence of an allele is detected in nucleic acid in the biological sample.

8. The method of claim 7, wherein the allele is detected by a method selected from the group consisting of allele specific oligonucleotide hybridization; size analysis; sequencing; hybridization; 5' nuclease digestion; single-stranded conformation polymorphism; allele specific hybridization; primer specific extension; and oligonucleotide ligation assay.

* * * * *

SEQUENCE LISTING

```
<160> NUMBER OF SEQ ID NOS: 2

<210> SEQ ID NO 1
<211> LENGTH: 185
<212> TYPE: PRT
<213> ORGANISM: Artificial Sequence
<220> FEATURE:
<223> OTHER INFORMATION: synthetic

<400> SEQUENCE: 1

Met Ala Phe Thr Glu His Ser Pro Leu Thr Pro His Arg Arg Asp Leu
 1               5                  10                  15

Ala Ser Arg Ser Ile Trp Leu Ala Arg Lys Ile Arg Ser Asp Leu Thr
                20                  25                  30

Ala Leu Thr Glu Ser Tyr Val Lys His Gln Gly Leu Asn Lys Asn Ile
            35                  40                  45

Asn Leu Asp Ser Ala Asp Gly Met Pro Val Ala Ser Thr Asp Arg Trp
    50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly
            180                 185

<210> SEQ ID NO 2
<211> LENGTH: 184
```

```
<212> TYPE: PRT
<213> ORGANISM: Artificial Sequence
<220> FEATURE:
<223> OTHER INFORMATION: Synthetic

<400> SEQUENCE: 2

Ala Phe Thr Glu His Ser Pro Leu Thr Pro His Arg Arg Asp Leu Ala
 1               5                  10                  15

Ser Arg Ser Ile Trp Leu Ala Arg Lys Ile Arg Ser Asp Leu Thr Ala
            20                  25                  30

Leu Thr Glu Ser Tyr Val Lys His Gln Gly Leu Asn Lys Asn Ile Asn
        35                  40                  45

Leu Asp Ser Ala Asp Gly Met Pro Val Ala Ser Thr Asp Arg Trp Ser
    50                  55                  60

Glu Leu Thr Glu Ala Glu Arg Leu Gln Glu Asn Leu Gln Ala Tyr Arg
65                  70                  75                  80

Thr Phe His Val Leu Leu Ala Arg Leu Leu Glu Asp Gln Gln Val His
                85                  90                  95

Phe Thr Pro Thr Glu Gly Asp Phe His Gln Ala Ile His Thr Leu Leu
                100                 105                 110

Leu Gln Val Ala Ala Phe Ala Tyr Gln Ile Glu Glu Leu Met Ile Leu
            115                 120                 125

Leu Glu Tyr Lys Ile Pro Arg Asn Glu Ala Asp Gly Met Pro Ile Asn
        130                 135                 140

Val Gly Asp Gly Gly Leu Phe Glu Lys Lys Leu Trp Gly Leu Lys Val
145                 150                 155                 160

Leu Gln Glu Leu Ser Gln Trp Thr Val Arg Ser Ile His Asp Leu Arg
                165                 170                 175

Phe Ile Ser Ser His Gln Thr Gly
            180
```